(12) United States Patent
Shibaya et al.

(10) Patent No.: US 9,687,035 B2
(45) Date of Patent: Jun. 27, 2017

(54) IMPACT-ABSORBING PAD, CLOTHING FURNISHED WITH SAME AND METHOD FOR PREVENTING FEMORAL FRACTURES

(75) Inventors: Miaki Shibaya, Settsu (JP); Eiichi Tanaka, Nagoya (JP); Sota Yamamoto, Tokyo (JP); Yosuke Mizuno, Osaka (JP)

(73) Assignees: KANEKA CORPORATION, Osaka-shi, Osaka (JP); NATIONAL UNIVERSITY CORPORATION NAGOYA UNIVERSITY, Nagoya-shi, Aichi (JP); SHIBAURA INSTITUTE OF TECHNOLOGY, Tokyo (JP)

( * ) Notice: Subject to any disclaimer, the term of this patent is extended or adjusted under 35 U.S.C. 154(b) by 400 days.

(21) Appl. No.: 13/820,346

(22) PCT Filed: Sep. 1, 2011

(86) PCT No.: PCT/JP2011/069929
§ 371 (c)(1),
(2), (4) Date: Jun. 27, 2013

(87) PCT Pub. No.: WO2012/029917
PCT Pub. Date: Mar. 8, 2012

(65) Prior Publication Data
US 2013/0298914 A1    Nov. 14, 2013

(30) Foreign Application Priority Data
Sep. 3, 2010    (JP) .................................. 2010-198101

(51) Int. Cl.
*A41D 31/00*    (2006.01)
*A41D 13/015*    (2006.01)
(Continued)

(52) U.S. Cl.
CPC ....... *A41D 31/0044* (2013.01); *A41D 13/015* (2013.01); *A41D 13/0506* (2013.01);
(Continued)

(58) Field of Classification Search
CPC .... A61F 2005/0193; A61F 5/30; A61F 13/06; A61F 2013/00272; A61F 2005/0183;
(Continued)

(56) References Cited

U.S. PATENT DOCUMENTS 5,557,804 A * 9/1996 Ovortrup ........... A41D 13/0506
                                                              128/888
5,943,694 A * 8/1999 Moureaux .......... A41D 31/0061
                                                                  2/2.5

(Continued)

FOREIGN PATENT DOCUMENTS

JP    9508824 A    9/1997
JP    09268409 A    10/1997
(Continued)

OTHER PUBLICATIONS

ISA Japan, International Search Report of PCT/JP2011/069929, Oct. 18, 2011, WIPO, 2 pages.

*Primary Examiner* — Kari Rodriquez
(74) *Attorney, Agent, or Firm* — Alleman Hall Creasman & Tuttle LLP

(57) ABSTRACT

To provide an impact-absorbing pad fully satisfying impact absorbability for preventing femoral neck fractures, wearing comfort and breathability not to cause discomfort for all-day use, a small thickness not to impair external appearance, and flexibility in a surface direction not to cause uncomfortable feeling at the time of putting on and taking off, which are required for the impact-absorbing pad used in a hip protector, clothing furnished with the impact-absorbing pad, and a method for preventing femoral fractures. A pad main body (Continued)

having impact absorbability includes an impact-deflecting part having a through hole or concavity with a maximum length of 80 mm or less and an area of 600 mm² or more and 5,000 mm² or less, and the pad main body is disposed so as to apply the impact-deflecting part onto the greater trochanter of the femur, thereby preventing femoral fractures.

12 Claims, 4 Drawing Sheets

(51) Int. Cl.
  *A41D 13/05* (2006.01)
  *A61F 5/01* (2006.01)
(52) U.S. Cl.
  CPC .... *A61F 5/0104* (2013.01); *A61F 2005/0181* (2013.01); *A61F 2005/0183* (2013.01)
(58) Field of Classification Search
  CPC ............ A41D 13/0506; A41D 13/0562; A41D 13/015; A41D 31/0044
  See application file for complete search history.

(56) References Cited

U.S. PATENT DOCUMENTS

| | | | |
|---|---|---|---|
| 6,093,468 A | * | 7/2000 | Toms ................. A41D 13/0158 2/22 |
| 6,334,443 B1 | * | 1/2002 | Olsen ................. A41D 13/0153 128/846 |
| 2009/0271918 A1 | | 11/2009 | Sorensen et al. |
| 2010/0192289 A1 | * | 8/2010 | Shibaya ............. A41D 31/0044 2/465 |
| 2012/0042486 A1 | * | 2/2012 | Dunn ...................... F16B 45/02 24/599.1 |

FOREIGN PATENT DOCUMENTS

| | | |
|---|---|---|
| JP | 09273582 A | 10/1997 |
| JP | 10237708 A | 9/1998 |
| JP | 2000290331 A | 10/2000 |
| JP | 2003175063 A | 6/2003 |
| JP | 2007291536 A | 11/2007 |
| JP | 3142546 U | 5/2008 |
| JP | 2009082697 A | 4/2009 |
| WO | 9519154 A1 | 7/1995 |

* cited by examiner

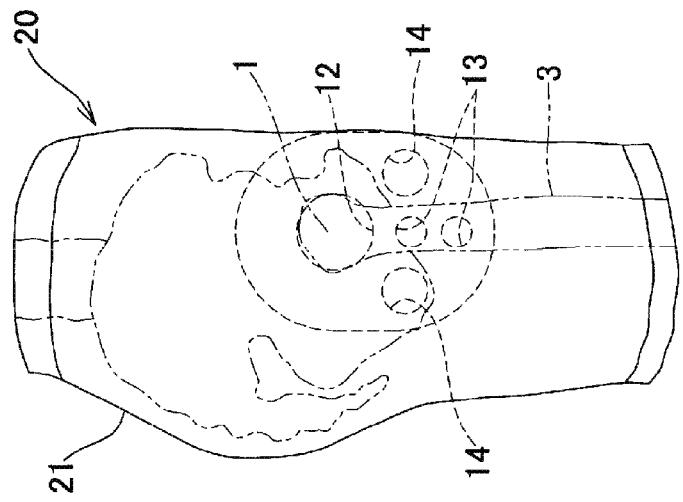
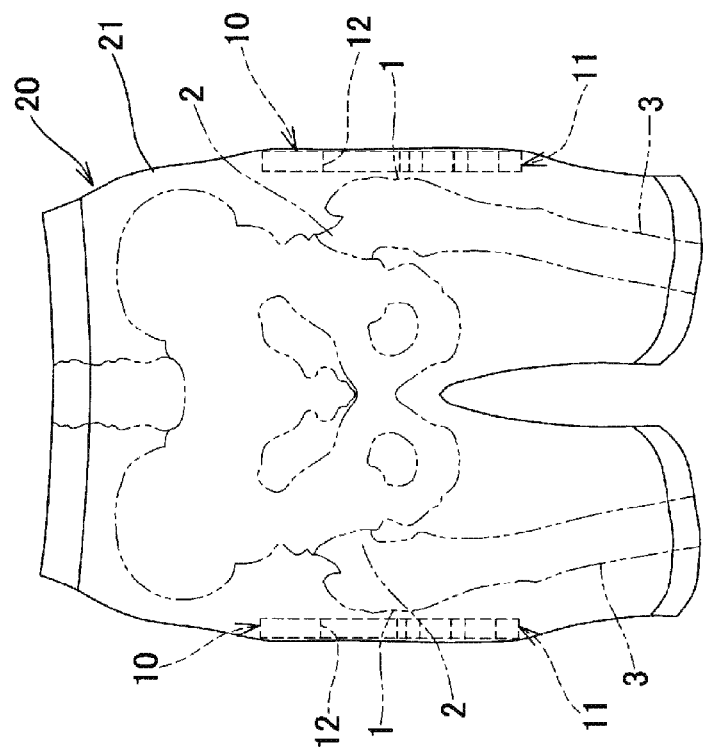

IMPACT-ABSORBING PAD, CLOTHING FURNISHED WITH SAME AND METHOD FOR PREVENTING FEMORAL FRACTURES

TECHNICAL FIELD

The present invention relates to an impact-absorbing material usable in order, for example, to prevent fractures in case of a fall, especially to prevent a patient with osteoporosis or others from breaking a bone in case of a fall, by furnishing the impact-absorbing material in clothing, especially in a suitable area around hips on underwear, clothing furnished with the impact-absorbing material, especially clothing such as underpants, and a method for preventing femoral fractures.

BACKGROUND ART

Fractures, especially femoral neck fractures due to a fall are known as one of the reasons why elderly people become bedridden (Non-Patent Document 1). Elderly people, especially elderly women have fragile bones due to osteoporosis or other reasons, and this increases the risk of fractures by a fall due to slight stumbling, by which young people would not break a bone. According to the survey on the estimated incidence of femoral neck fractures (Non-Patent Document 2), the yearly incidence of femoral neck fractures more than doubled, from 53,200 people in 1987 to 148,100 people in 2007, reflecting aging population. It is significant to prevent the incidence as well as to treat fractures from the viewpoint of increase in medical cost and QOL of elderly people. Examples of interventions with evidence to prevent femoral neck fractures include the administration of pharmaceutical drugs for increasing bone density and a hip protector as a protective equipment (Non-Patent Document 3). The hip protector is applied to elderly people having such a high fall risk that they may fall at any time, and thus is required to be used all day.

For example, a hip protector including a dome-shaped member (Patent Document 1) includes a hard resin such as a polypropylene foam. The hard pad is of external force diffusion type, which increases an area to which external force is applied and simultaneously reduces external force due to the material elasticity, resulting in excellent impact absorbability. However, a hip protector using the hard pad has poor wearing comfort. Hence, a person may take off the hip protector consciously or unconsciously, for example, at bedtime and then may fall to break a bone. Meanwhile, in order to improve wearing comfort, a soft pad including an acrylic polymer has been developed (Patent Document 2). Such a soft pad is of external force absorption type. External force is heat transformed by deformation of the material and is consequently reduced. A hip protector using the soft pad has improved wearing comfort as compared with that using the hard pad but has low impact absorbability, which increases the pad thickness. When a person wears a protector using such a soft pad, the pad shape can be recognized by the external appearance even when the person wears clothing on the protector. Elderly women worrying about their appearance are difficult to accept such a protector. In addition, the pad has insufficient breathability.

A hip protector typically has the shape of underwear such as underpants because it is required to be worn all day. A hard pad and even a soft pad having poor flexibility in a surface direction are often difficult to be put on and taken off in a bathroom or in the time of changing clothes. In a nursing home or other institution, a caregiver may help a person to put on and take off a protector in a bathroom, but a conventional hip protector is unfavorable for the caregiver because the hip protector is difficult to be put on and taken off.

A pad used in a hip protector is required to have impact absorbability for preventing femoral neck fractures, wearing comfort and breathability not to cause discomfort for all-day use, a small thickness not to impair external appearance, and flexibility in a surface direction not to cause uncomfortable feeling at the time of putting on and taking off the hip protector. However, there is actually no pad satisfying all the requirements at the present time.

Citation list

Patent Literatures

Patent Document 1: JP-A No. 9-508824
Patent Document 2: JP-A No. 9-268409

Non-Patent Literatures

Non-Patent Document 1: J. B. Lauritzen, Yasushi Hayashi, Hajime Orimo: Prevention of Bone Fractures in Falling by Hip Protector, Osteoporosis Japan, 10: 149-157, 2002

Non-Patent Document 2: Fifth National Survey on the Incidence of Femoral Neck Fractures Non-Patent Document 3: Atsushi Harada: Musculoskeletal Ambulation Disability Symptom Complex and Development in the Future, Orthopedic and Accident Surgery (Seikei Saigai Geka), 50: 27-35, 2007

SUMMARY OF INVENTION

Technical Problem

It is an object of the present invention to provide an impact-absorbing pad fully satisfying impact absorbability for preventing femoral neck fractures, wearing comfort and breathability not to cause discomfort for all-day use, a small thickness not to impair external appearance, and flexibility in a surface direction not to cause uncomfortable feeling at the time of putting on and taking off, which are required for the impact-absorbing pad used in a hip protector, clothing furnished with the impact-absorbing pad, and a method for preventing femoral fractures.

Solution to Problem

An impact-absorbing pad of the present invention includes a pad main body having impact absorbability, the pad main body including an impact-deflecting part having a through hole or concavity with a maximum length of 80 mm or less and an area of 600 $mm^2$ or more and 5,000 $mm^2$ or less, the pad main body being disposed to apply the impact-deflecting part onto the greater trochanter of the femur, thereby preventing a femoral fracture.

By installing the impact-absorbing pad on a side face of a body corresponding to a side of the greater trochanter of the femur so that the impact-deflecting part of the impact-absorbing pad faces the greater trochanter of the femur, the pad main body and a periphery of the greater trochanter of the femur facing the pad main body absorb impact force to the greater trochanter of the femur in case of a fall or the like, and the impact-deflecting part prevents the greater trochanter of the femur from being directly affected by the impact force. The impact-absorbing pad can therefore effectively prevent femoral neck fractures. When the impact-deflecting part has a length of more than 80 mm, the greater trochanter of the femur protrudes from a pad main body having such an impact-deflecting part to the outside and the impact force in case of a fall may directly affect the greater trochanter of the femur. Hence, the impact-deflecting part is designed to have a length of 80 mm or less. In order to dispose the pad main body while surrounding the greater trochanter of the femur, the impact-deflecting part is designed to have an area of 600 mm$^2$ or more and 5,000 mm$^2$ or less. The impact-deflecting part preferably includes a through hole but may include a concavity. An impact-absorbing pad including an impact-deflecting part having a concavity is installed so that an opening side of the concavity faces the greater trochanter of the femur. The inside of the impact-deflecting part preferably includes a cavity for weight reduction and improvement in breathability, but an impact-deflecting part filled with a softer member than the pad main body is included in the present invention. The impact-deflecting part can include a plurality of long slit-like through holes or concavities that have a total area of 600 mm$^2$ or more and 5,000 mm$^2$ or less. The inner peripheral face of the impact-deflecting part may be a taper face in which the inner diameter of the impact-deflecting part gradually increases with increasing proximity to the installation face to a body. This reduces impact force continuously or stepwise with increasing proximity to the greater trochanter of the femur.

Here, in a preferred aspect, the pad main body is designed to have a thickness of 13 mm or less. When the pad main body has a thickness of more than 13 mm, the line of an impact-absorbing pad including such a pad main body is exposed to the surface of clothing to impair the external appearance of the clothing and the impact-absorbing pad has lowered flexibility in a surface direction to reduce wearing comfort. Thus, the thickness is preferably designed to be 13 mm or less.

It is preferable that a distance from an upper end of the impact-deflecting part to an upper end of the pad main body be designed to be 10 mm or more. When the distance is less than 10 mm, such a pad main body has reduced absorption effect of impact force and reduced diffusion effect of impact force thereby not to sufficiently ensure the impact absorbability. Hence, the distance is preferably designed to be 10 mm or more. In the description below in the present specification, in an impact-absorbing pad applied on a human body, a head side of the human body is defined as an upper side, while a foot side is defined as a lower side.

In another preferred aspect, the pad main body includes at least one first relief part having a through hole or concavity below the impact-deflecting part, a distance from a lower end of the impact-deflecting part to an upper end of the first relief part is 5 mm or more and 50 mm or less, and the first relief part is designed to have a maximum length of 5 mm or more and 50 mm or less. In this case, the first relief part prevents the upper part of the shaft of the femur from being affected by large impact force, thereby further effectively preventing femoral neck fractures. In addition, the first relief part can improve breathability to reduce stuffy feeling, enables the impact-absorbing pad to be lightweight, heightens the flexibility of the pad main body, and can reduce uncomfortable feeling at the time of putting on and taking off the pad.

In a preferred aspect, two first relief parts are arranged vertically. In such a structure, one impact-deflecting part and two first relief parts are arranged vertically. This can improve the flexibility of the pad main body on the vertical line passing through the impact-deflecting part and the first relief parts as the center, thereby further effectively reducing uncomfortable feeling at the time of putting on and taking off the pad.

In another preferred aspect, the pad main body includes a second relief part having at least one through hole or concavity, and the second relief part has an area of 50% or less of a total area of the pad main body except the impact-deflecting part and the first relief part. In this case, the second relief part can further improve the breathability to reduce the stuffy feeling, enable the impact-absorbing pad to be lightweight, heighten the flexibility of the pad main body, and can further reduce the uncomfortable feeling at the time of putting on and taking off the pad.

In a preferred aspect, the pad main body includes an elastomer, and the elastomer is an isobutylene block copolymer including a polymer block having isobutylene as a constituent monomer and a polymer block having an aromatic vinyl monomer as a constituent monomer. In this case, a pad main body including such a material is preferred because it has excellent impact absorbability in a wide temperature range.

In a preferred aspect, the elastomer contains a tackifier resin. In this case, a pad main body including such a material is preferred because the tackifier resin can increase the impact absorbability of the elastomer around body temperature.

In a preferred aspect, the pad main body includes an elastomer foam. In this case, such a pad main body is preferred because the impact absorbability of the pad main body can be easily improved.

Clothing of the present invention includes the impact-absorbing pad, and the impact-absorbing pad is attached to a main body of the clothing to apply the impact-deflecting part of the impact-absorbing pad onto the greater trochanter of the femur.

In the clothing, the impact-absorbing pad is attached to a main body of the clothing so that the impact-deflecting part of the impact-absorbing pad is applied onto the greater trochanter of the femur. Hence, as with the impact-absorbing pad above, the pad main body and a periphery of the greater trochanter of the femur facing the pad main body absorb impact force to the greater trochanter of the femur in case of a fall or the like, and the impact-deflecting part prevents the greater trochanter of the femur from being directly affected by the impact force. The clothing can therefore effectively prevent femoral neck fractures.

Here, in a preferred aspect, the impact-absorbing pad is removably attached to the clothing main body. In this case, the impact-absorbing pad can be removed from the clothing main body and the clothing main body can be washed. This enables the expensive impact-absorbing pad to be used in a plurality of clothing, thereby reducing the economic burden on a user.

It is preferable that the clothing main body be underpants. The underpants are disposed so as to cover the greater trochanter of the femur and thus are preferred to attach the impact-absorbing pad.

A method for preventing a femoral fracture of the present invention includes attaching the impact-absorbing pad to apply the impact-deflecting part of the impact-absorbing pad onto the greater trochanter of the femur.

In the method for preventing a femoral fracture, the impact-absorbing pad is attached so as to apply the impact-deflecting part of the impact-absorbing pad onto the greater trochanter of the femur. Hence, as with the impact-absorbing pad above, the pad main body and a periphery of the greater trochanter of the femur facing the pad main body absorb impact force to the greater trochanter of the femur in case of a fall or the like, and the impact-deflecting part prevents the greater trochanter of the femur from being directly affected by the impact force. The method can therefore effectively prevent femoral neck fractures.

Advantageous Effects of Invention

By the impact-absorbing pad of the present invention, the clothing furnished with the impact-absorbing pad, and the method for preventing femoral fractures, the impact-deflecting part is disposed in the impact-absorbing pad so as to contain a region corresponding to the greater trochanter of the femur. This can prevent femoral neck fractures of elderly people due to a fall while maintaining a small thickness not to impair wearing comfort and external appearance. The first relief part further provided below the impact-deflecting part can ensure breathability, and the second relief parts provided on right and left sides of the first relief part can maintain the flexibility in the vertical direction of the pad and can eliminate uncomfortable feeling at the time of putting on and taking off the impact-absorbing pad.

BRIEF DESCRIPTION OF THE DRAWINGS

FIG. 2(a) is a front view of a piece of clothing furnished with the impact-absorbing pad and FIG. 2(b) is a side view thereof.

DESCRIPTION OF EMBODIMENTS

Embodiments of the present invention will be described in detail hereinafter with reference to drawings. The present embodiments will be described while defining the relative position on the basis of an impact-absorbing pad in FIG. 1.

Figure 1:
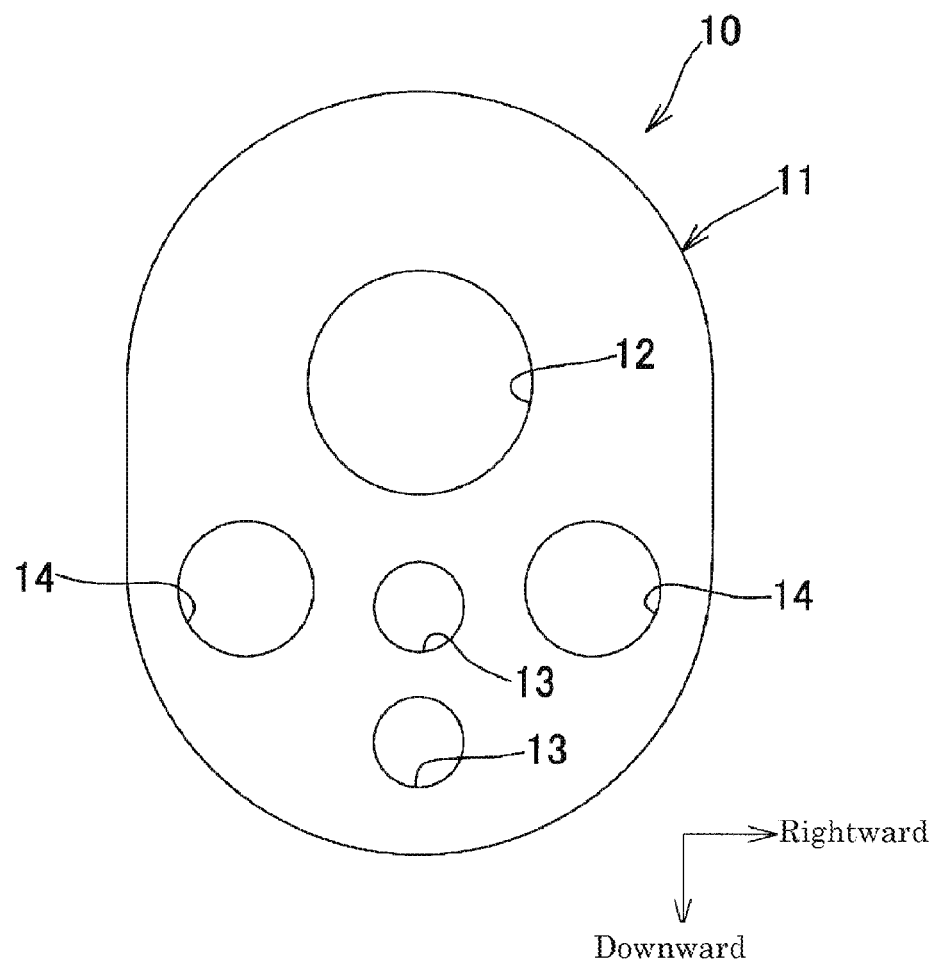
FIG. 1 is a front view of an impact-absorbing pad.
Figure 3A:
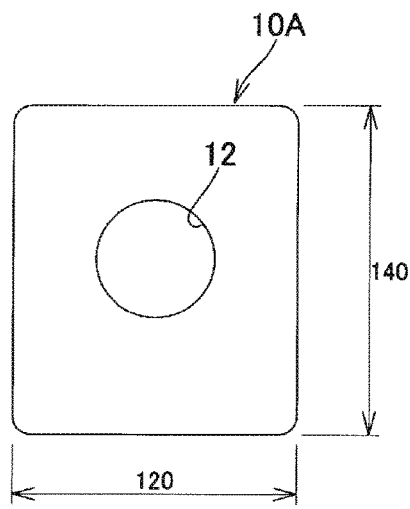
FIGS. 3(a) to (d) are front views of impact-absorbing pads of Examples.
Figure 3B:
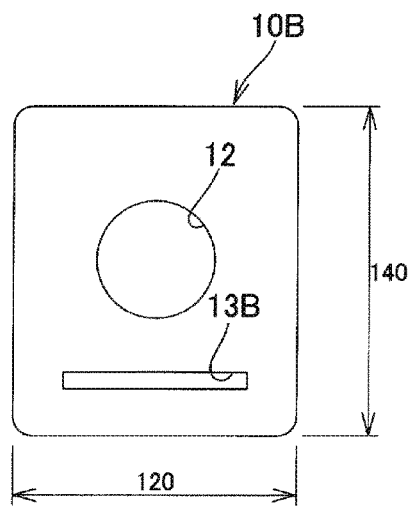
Figure 3C:
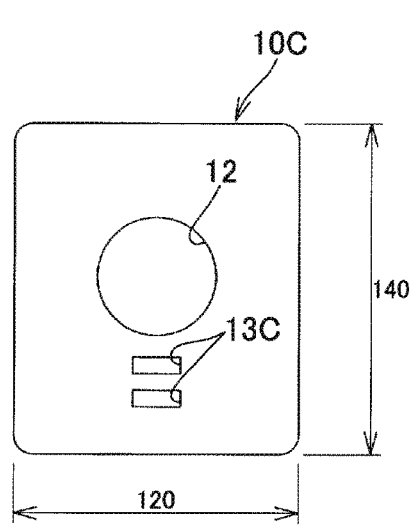
Figure 3D:
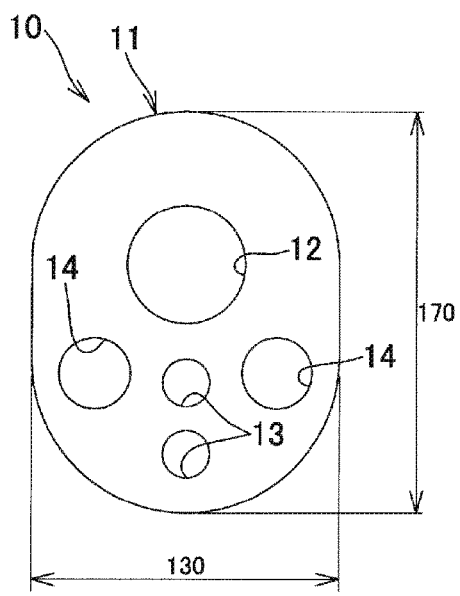
Figure 4A:
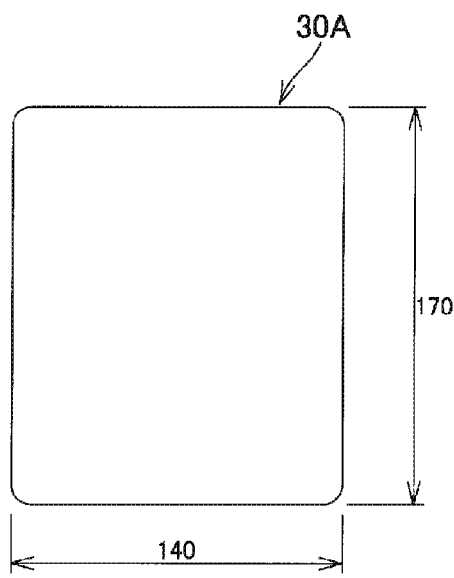
FIGS. 4(a) to (d) are front views of impact-absorbing pads of Comparative Examples.
Figure 4B:
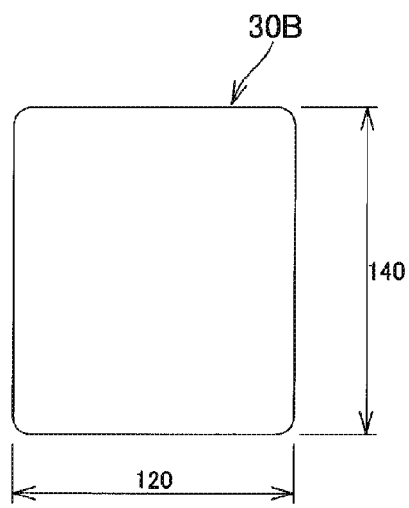
Figure 4C:
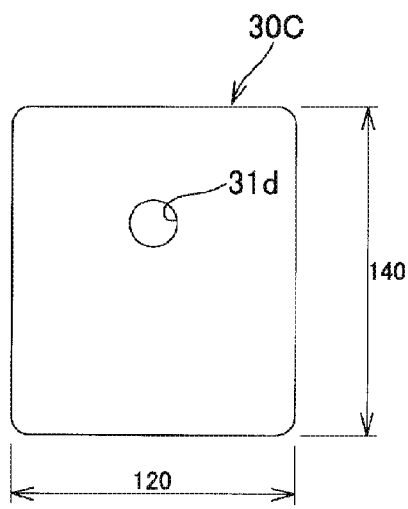
Figure 4D:
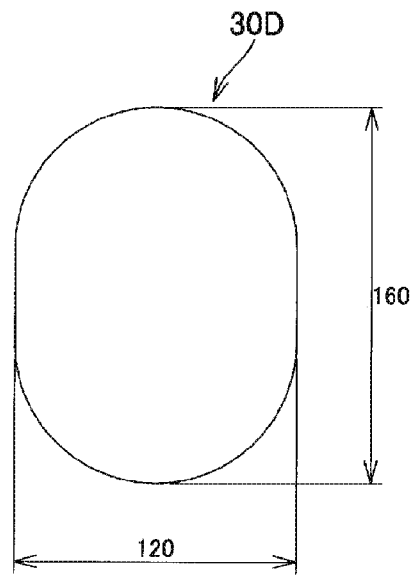

As shown in FIG. 1 and FIG. 2, an impact-absorbing pad 10 includes a pad main body 11 having impact absorbability. The pad main body 11 includes an impact-deflecting part 12 having a through hole or concavity with a maximum length of 80 mm or less and an area of 600 mm$^2$ or more and 5,000 mm$^2$ or less, and the impact-absorbing pads 10 is disposed on each side of a body so that the impact-deflecting part 12 is applied onto the greater trochanter 1 of the femur, thereby preventing fractures of the femoral neck 2.

An impact-absorbing pad that has no impact-deflecting part 12 having a through hole or concavity corresponding to the greater trochanter 1 of the femur transfers impact force due to a fall from the pad main body 11 through the greater trochanter 1 of the femur to the femoral neck 2 except the case where the pad main body 11 has a sufficient thickness. This may cause fractures. Meanwhile, an impact-absorbing pad that includes a pad main body 11 having a sufficient thickness so as not to transfer impact force to the femoral neck 2 impairs wearing comfort and external appearance. To address this, in the present invention, the impact-deflecting part 12 is provided in a region corresponding to the greater trochanter 1 of the femur, thereby diffusing impact force to surrounding soft tissues. This prevents the greater trochanter 1 of the femur from being directly affected by the impact, and consequently achieves the impact-absorbing pad 10 having such a small thickness that wearing comfort and external appearance are not impaired.

When the impact-deflecting part 12 has a maximum length of more than 80 mm, the top of the greater trochanter 1 of the femur protrudes from the pad main body 11 to the outside, and the impact force in case of a fall may directly affect the greater trochanter 1 of the femur. Hence, the impact-deflecting part 12 is designed to have a length of 80 mm or less. The impact-deflecting part 12 preferably has an area of 600 mm$^2$ or more and 5,000 mm$^2$ or less so as to dispose the pad main body 11 around the greater trochanter 1 of the femur. More preferably, the maximum length is 60 mm or less and the area is 700 mm$^2$ or more and 4,000 mm$^2$ or less. Even more preferably, the maximum length is 60 mm or less and the area is 700 mm$^2$ or more and 2,000 mm$^2$ or less.

The impact-deflecting part 12 may include a through hole or a non-penetration concavity but preferably includes a through hole from the viewpoint of breathability. An impact-absorbing pad 10 including an impact-deflecting part 12 having a concavity is disposed so that an opening of the concavity faces the greater trochanter 1 of the femur. The impact-deflecting part 12 may include a groove-like concavity elongated in the vertical direction or the horizontal direction.

Examples of the shape of the impact-deflecting part 12 include, but are not necessarily limited to, a round shape, an elliptical shape, a triangular shape, a rectangular shape, a polygonal shape, a gourd shape, a cross shape, an arch shape, a moon shape, a rounded quadrangular shape, and a rounded polygonal shape. The shape is preferably a round shape or an elliptical shape and is more preferably a round shape. The inner peripheral face of the impact-deflecting part 12 is preferably formed into a cylindrical shape, but may be formed into a taper face in which the inner diameter of the impact-deflecting part gradually increases with increasing proximity to the attachment face to a body, thereby reducing impact force continuously or stepwise with increasing proximity to the greater trochanter 1 of the femur.

Disposing the pad main body 11 so as to apply the impact-deflecting part 12 onto the greater trochanter 1 of the femur means that, as shown in FIG. 2, the pad main body 11 is disposed on a body surface so that the impact-deflecting part 12 faces the greater trochanter 1 of the femur. The impact-deflecting part 12 can be disposed so as to partially contain the region in a body surface facing the greater trochanter 1 of the femur, but is preferably disposed so as to wholly contain the region in a body surface facing the greater trochanter 1 of the femur so that impact force does not affect the greater trochanter 1 of the femur through the pad main body 11.

Examples of the shape of the pad main body 11 include, but are not necessarily limited to, a circular shape, an elliptical shape, polygonal shapes such as a rectangular shape and a diamond shape, and a shape having any uneven surface. The pad main body 11 may appropriately have through openings for breathability. The shape is preferably a rectangular shape or an elliptical shape. Among them, an elliptical shape is more preferred from the viewpoint of easy installation.

A pad main body 11 having an excessively large thickness exposes the line of the pad main body 11 to the surface of clothing to impair the external appearance of the clothing and has reduced flexibility in a surface direction of the pad main body 11 to lower wearing comfort. Hence, the thickness is preferably designed to be 13 mm or less, more preferably 10 mm or less, and even more preferably 8 mm or less in order to improve wearing comfort and to eliminate funny external appearance. Here, the thickness of a pad main body 11 means the maximum thickness of the pad main body 11. The pad main body 11 may have a flat shape with a uniform thickness, may have a shape having a central part with a large thickness and having an end part with a small thickness, or may have a shape with a thickness varying depending on a position. In a preferred embodiment, a chamfered face is formed on at least a corner of the outer peripheral edge on the outer surface of the pad main body 11. When the pad main body 11 is installed in clothing such as underpants, an area in the clothing with which a corner of the outer peripheral edge of the pad main body 11 is in contact is spread to have a reduced thickness, and the area is likely to be torn by rubbing due to, for example, friction with layered clothes. In order to prevent this, the pad main body 11 preferably has a chamfered face on at least a corner of the outer peripheral edge on the outer surface. The chamfered face may include a slope face or an arc face. The chamfered face is preferably formed along the entire outer peripheral edge of the pad main body 11, but may be partially formed. The formation region of the chamfered face in the thickness direction of the pad main body 11 can be arbitrarily designed. The chamfered face may be formed along the entire outer peripheral thickness of the pad main body 11. When the pad main body 11 is produced by a core back method, the chamfered face can be formed in a region having about a half or less of the outer peripheral thickness of the pad main body 11. In addition to the outer peripheral edge of the pad main body 11, a chamfered face can also be formed on at least a corner of the opening edge on the outer surface of the impact-deflecting part 12.

The distance from the upper end of the impact-deflecting part 12 to the upper end of the pad main body 11 is preferably designed to be 10 mm or more, more preferably 20 mm or more, and even more preferably 35 mm or more in order to effectively diffuse impact force.

At least one first relief part 13 having a through hole or concavity is preferably provided below the impact-deflecting part 12. The distance between the lower end of the impact-deflecting part 12 and the upper end of the first relief part 13 is designed to be 5 mm or more and 50 mm or less, preferably 10 mm or more and 40 mm or less, and most preferably 10 mm or more and 30 mm or less in order to reduce impact force applied to the greater trochanter 1 of the femur. The first relief part 13 provided in addition to the impact-deflecting part 12 achieves the improvement in flexibility in a surface direction of the pad main body 11, thereby to reduce uncomfortable feeling at the time of putting on and taking off, and achieves the improvement in breathability to reduce stuffy feeling. In addition, the first relief part 13 provided changes a route transmitting impact force in case of a fall, and this can reduce the impact force transmitted to the femoral neck 2.

The first relief part 13 may include a through hole or non-penetration concavity but preferably includes a through hole from the viewpoint of breathability. An impact-absorbing pad 10 including a first relief part 13 having a concavity is disposed so that an opening of the concavity faces the greater trochanter 1 of the femur. The first relief part 13 is preferably designed to have a diameter of 5 mm or more and 50 mm or less, more preferably a diameter of 5 mm or more and 40 mm or less, and most preferably a diameter of 5 mm or more and 30 mm or less from the viewpoint of, for example, strength of the pad main body 11.

As with the impact-deflecting part 12, examples of the shape of the first relief part 13 include, but are not necessarily limited to, a round shape, an elliptical shape, a triangular shape, a rectangular shape, a polygonal shape, a gourd shape, a cross shape, an arch shape, a moon shape, a rounded quadrangular shape, and a rounded polygonal shape. The shape is more preferably a round shape, an elliptical shape, or a rectangular shape. The shape is even more preferably a round shape or a rectangular shape. The number of the first relief part 13 may be one to eight.

As shown in FIG. 1, two first relief parts 13 are preferably arranged vertically below the impact-deflecting part 12. The arrangement position and the number of the first relief parts 13 are not necessarily limited, but preferably, a first relief part 13 having a round shape with a diameter of 20 mm is provided so as to have the upper end at a position 20 mm distant from the lower end of the impact-deflecting part 12, and another first relief part 13 with a diameter of 20 mm is provided so as to have the upper end at a position 10 mm distant from the lower end of the first relief part 13 above.

The pad main body 11 may have at least one second relief part 14 that has an area of 50% or less of the total area of the pad main body 11 except the impact-deflecting part 12 and the first relief part 13. The second relief part 14 may include a through hole or non-penetration concavity but preferably includes a through hole from the viewpoint of breathability. The arrangement position and the number of the second relief part 14 are not necessarily limited. For example, at least one second relief part 14 is preferably provided in the horizontal direction of the first relief part 13. More preferably, a total of two second relief parts may be provided on right and left sides, as shown in FIG. 1, from the viewpoint of ensuring breathability and flexibility in a surface direction. In order to improve the breathability, the pad main body 11 may have small holes having an area of 50% or less of the total area at any positions except the impact-deflecting part 12 and the first relief part 13 as long as the impact absorbability is not lowered.

A material constituting the pad main body 11 preferably has a flexural modulus of 100 MPa or less that is calculated based on the measurement in accordance with JIS K7171, from the viewpoint of wearing comfort. The flexural modulus is more preferably 50 MPa or less. The flexural modulus is even more preferably 20 MPa or less in order to reduce resistance feeling at the time of putting on and taking off.

An elastomer constituting the pad main body is preferably an isobutylene block copolymer that includes a polymer block having an aromatic vinyl compound as a constituent monomer and a polymer block having an aliphatic hydrocarbon compound as a constituent monomer.

Examples of the structure of the polymer block include a triblock copolymer including a polymer block having an aromatic vinyl compound as a constituent monomer/a polymer block having an aliphatic hydrocarbon compound as a constituent monomer/a polymer block having an aromatic vinyl compound as a constituent monomer, a diblock copolymer including a polymer block having an aromatic vinyl compound as a constituent monomer/a polymer block having an aliphatic hydrocarbon compound as a constituent monomer, and a star block copolymer including three or more arms made of a polymer block having an aromatic vinyl compound as a constituent monomer and a polymer block having an aliphatic hydrocarbon compound as a constituent monomer. These copolymers can be used singly or in combination of two or more of them in order to achieve desired physical properties and moldability.

The weight ratio of the polymer block having an aromatic vinyl compound as a constituent monomer and the polymer block having an aliphatic hydrocarbon compound as a constituent monomer is not particularly limited. However, from the viewpoint of impact absorbability, moldability, and shape retention properties at an ordinary temperature of a foam, the ratio of (polymer block having an aliphatic hydrocarbon compound as a constituent monomer)/(polymer block having an aromatic vinyl compound as a constituent monomer) is preferably 95/5 to 60/40 (weight ratio) and more preferably 90/10 to 65/35 (weight ratio).

Examples of the aromatic vinyl compound include, but are not necessarily limited to, styrene, o-, m-, or p-methylstyrene, α-methylstyrene, β-methylstyrene, 2,6-dimethylstyrene, 2,4-dimethylstyrene, α-methyl-o-methylstyrene, α-methyl-m-methylstyrene, α-methyl-p-methylstyrene, β-methyl-o-methylstyrene, β-methyl-m-methylstyrene, β-methyl-p-methylstyrene, 2,4,6-trimethylstyrene, α-methyl-2,6-dimethylstyrene, α-methyl-2,4-dimethylstyrene, β-methyl-2,6-dimethylstyrene, β-methyl-2,4-dimethylstyrene, o-, m-, or p-chlorostyrene, 2,6-dichlorostyrene, 2,4-dichlorostyrene, α-chloro-o-chlorostyrene, α-chloro-m-chlorostyrene, α-chloro-p-chlorostyrene, β-chloro-o-chlorostyrene, β-chloro-m-chlorostyrene, β-chloro-p-chlorostyrene, 2,4,6-trichlorostyrene, α-chloro-2,6-dichlorostyrene, α-chloro-2,4-dichlorostyrene, β-chloro-2,6-dichlorostyrene, β-chloro-2,4-dichlorostyrene, o-, m-, or p-t-butylstyrene, o-, m-, or p-methoxystyrene, o-, m-, or p-chloromethylstyrene, o-, m-, or p-bromomethylstyrene, styrene derivatives substituted with a silyl group, indene, and vinylnaphthalene. These compounds may be used singly or in combination of two or more of them. Among them, at least one compound selected from the group consisting of styrene, p-methylstyrene, α-methylstyrene, and indene is desired from the viewpoint of easy availability and physical property balance. By polymerization of such an aromatic vinyl compound as a main component, the polymer block having an aromatic vinyl compound as a constituent monomer can be formed.

The polymer block having an aliphatic hydrocarbon compound as a constituent monomer is preferably a polymer block having a conjugated diene as a main component. Examples of the conjugated diene include, but are not necessarily limited to, 1,3-butadiene, isoprene, chloroprene, and 2,3-dimethyl-1,3-butadiene. These dienes may be used singly or in combination of two or more of them. Among them, at least one diene selected from the group consisting of 1,3-butadiene and isoprene is desired from the viewpoint of easy availability and physical property balance. The polymer block having a conjugated diene as a main component may be hydrogenated or may be copolymerized with a vinyl compound except the conjugated diene, as necessary.

Among the polymer blocks having a conjugated diene as a main component, one of a block in which a conjugated diene is polymerized so that a 3,4- or 1,2-bond is included in a large amount, a hydrogenated block of the conjugated diene polymer, and a polymer block having isobutylene as a main component is preferred due to excellent impact absorbability around room temperature. Among them, a polymer block having a conjugated diene that contains the bond in a large amount, as a main component is likely to reduce impact absorbability in a temperature region out of a certain temperature region. Specifically the polymer block having isobutylene as a main component is particularly preferred because it has excellent impact absorbability in a wide temperature range.

In the polymer block having isobutylene as a main component, an additional vinyl compound may be copolymerized, as necessary.

When the polymer block having an aliphatic hydrocarbon compound as a constituent monomer is the polymer block having isobutylene as a main component, the method for producing an elastomer is not particularly limited. For example, a monomer component containing isobutylene as a main component and a monomer component containing an aromatic vinyl monomer as a main component are polymerized in the presence of a compound of General Formula (1) to afford an elastomer.

$$(CR^1R^2X)_nR^3 \quad (1)$$

[In the formula, X is a halogen atom, an alkoxy group having 1 to 6 carbon atoms, or an acyloxy group having 1 to 6 carbon atoms. Each of $R^1$ and $R^2$ is a hydrogen atom or a monovalent hydrocarbon group having 1 to 6 carbon atoms and $R^1$ and $R^2$ may be the same as or different from each other. $R^3$ is a polyvalent aromatic hydrocarbon group or a polyvalent aliphatic hydrocarbon group, and n is a natural number of 1 to 6]

The compound of General Formula (1) is an initiator, which generates a carbocation in the presence of a Lewis acid or others and is believed to be a start point of cationic polymerization. Examples of the compound of General Formula (1) usable in the present invention include compounds such as:

(1-chloro-1-methylethyl)benzene, 1,4-bis(1-chloro-1-methylethyl)benzene, 1,3-bis(1-chloro-1-methylethyl)benzene, 1,3,5-tris(1-chloro-1-methylethyl)benzene, and 1,3-bis(1-chloro-1-methylethyl)-5-(tert-butyl)benzene.

Among them, 1,4-bis(1-chloro-1-methylethyl)benzene and 1,3,5-tris(1-chloro-1-methylethyl)benzene are specifically preferred.

In the polymerization, a Lewis acid catalyst may be used in combination. A Lewis acid usable for cationic polymerization may be used, and metal halides such as $TiCl_4$, $TiBr_4$, $BCl_3$, $BF_3$, $BF_3$—$OEt_2$, $SnCl_4$, $SbCl_5$, $SbF_5$, $WCl_6$, $TaCL_5$, $VCl_5$, $FeCl_3$, $ZnBr_2$, $AlCl_3$, and $AlBr_3$; and organic metal halides such as $Et_2AlCl$ and $EtAlCl_2$ can be suitably used (Et represents an ethyl group). Among them, $TiCl_4$, $BCl_3$, and $SnCl_4$ are preferred considering catalytic ability and industrially easy availability.

The amount of a Lewis acid used is not particularly limited and can be designed depending on the polymerization characteristics of a monomer to be used, polymerization concentration, and other factors. Commonly, a Lewis acid is preferably used in a range of 0.1 molar equivalent or more and 100 molar equivalents or less with respect to the compound of General Formula (1) and more preferably in a range of 1 molar equivalent or more and 50 molar equivalents or less.

In the polymerization, an electron donor component may further be used in combination, as necessary. The electron donor component is considered to have the effect of stabilizing growing carbocations during cationic polymerization, and the addition of the electron donor enables the formation of a polymer that has a narrow molecular weight distribution and a controlled structure. Examples of the electron donor component usable include, but are not necessarily limited to, pyridines, amines, amides, sulfoxides, esters, and metal compounds having an oxygen atom bonded to a metal atom.

The polymerization may be carried out in an organic solvent, as necessary, and any organic solvents can be used as long as cationic polymerization is not substantially inhibited. Specific examples of the organic solvent include halogenated hydrocarbons such as methyl chloride, dichloromethane, chloroform, ethyl chloride, dichloroethane, n-propyl chloride, n-butyl chloride, and chlorobenzene; alkylbenzenes such as benzene, toluene, xylene, ethylbenzene, propylbenzene, and butylbenzene; straight-chain aliphatic hydrocarbons such as ethane, propane, butane, pentane, hexane, heptane, octane, nonane, and decane; branched aliphatic hydrocarbons such as 2-methylpropane, 2-methylbutane, 2,3,3-trimethylpentane, and 2,2,5-trimethylhexane; cyclic aliphatic hydrocarbons such as cyclohexane, methylcyclohexane, and ethylcyclohexane; and paraffin oils obtained by hydrogenation and purification of a petroleum fraction.

These solvents may be used singly or in combination of two or more of them, considering the balance of the polymerization characteristics of monomers constituting the block copolymer, the solubility of a polymer to be formed, and other factors.

The amount of the solvent used can be determined so that the concentration of a polymer is preferably 1% by weight or more and 50% by weight or less and more preferably 5% by weight or more and 35% by weight or less, considering the viscosity of a polymer solution to be obtained and the easiness of removing heat.

For an actual polymerization, each component is preferably mixed while cooling, for example, at a temperature of −100° C. or more and 0° C. or less. In order to equilibrate energy cost with polymerization stability, the temperature range is particularly preferably −80° C. or more and −30° C. or less.

As commercially available elastomers usable in the present invention, HYBRAR manufactured by Kuraray Co., Ltd. can be exemplified as the elastomer in which the polymer block having an aliphatic hydrocarbon compound as a constituent monomer is a polymer block having a conjugated diene as a main component, and SIBSTAR manufactured by Kaneka Corporation can be exemplified as the elastomer in which the polymer block is a polymer block having isobutylene as a main component.

The elastomer constituting the impact-absorbing pad 10 of the present invention may further contain a tackifier resin. The tackifier resin used in the present invention is a low molecular weight resin having a number average molecular weight of 300 or more and 3,000 or less and a softening point of 60° C. or more and 150° C. or less determined by a ring and ball method in accordance with JIS K-2207. An elastomer containing the tackifier resin readily enables the impact absorbability to be increased around body temperature.

Examples of the tackifier resin in the present invention include rosin and rosin derivatives, polyterpene resins, aromatic modified terpene resins and hydrogenated products of them, terpene phenol resins, coumarone-indene resins, aliphatic petroleum resins, alicyclic petroleum resins and hydrogenated products of them, aromatic petroleum resins and hydrogenated products of them, aliphatic aromatic copolymerized petroleum resins and hydrogenated products of them, dicyclopentadiene petroleum resins and hydrogenated products of them, and low molecular weight polymers of styrene or a substituted styrene. Among them, alicyclic petroleum resins and hydrogenated products of them, aliphatic petroleum resins, hydrogenated products of aromatic petroleum resins, polyterpene resins, dicyclopentadiene petroleum resins, rosin, and other resins are particularly preferred because they have high compatibility with the polymer block having an aliphatic hydrocarbon compound as a main component in the elastomer.

The amount of the tackifier resin is preferably 0 part by weight or more and 100 parts by weight or less and more preferably 10 parts by weight or more and 70 parts by weight or less with respect to 100 parts by weight of the elastomer. A tackifier in an amount of more than 100 parts by weight leads to excessively low viscosity during kneading, resulting in insufficient kneading. This may make the preparation of a good foam difficult.

The elastomer in the present invention may further contain a plasticizer, as necessary. The plasticizer is not particularly limited and commonly, a liquid material or a material in a liquid form at room temperature is suitably used. Both hydrophilic plasticizers and hydrophobic plasticizers can be used. Examples of such a plasticizer include various plasticizers for rubber or resin, such as mineral oil plasticizers, vegetable oil plasticizers, and synthetic plasticizers.

Examples of the mineral oil plasticizer include process oils such as naphthenic process oil and paraffinic process oil; examples of the vegetable oil plasticizer include castor oil, cottonseed oil, linseed oil, rapeseed oil, soybean oil, palm oil, coconut oil, peanut oil, Japan wax, pine oil, and olive oil; and examples of the synthetic plasticizer include polybutene and low molecular weight polybutadiene. Among them, paraffinic process oil or polybutene is preferably used from the viewpoint of compatibility with the elastomer. Two or more of these plasticizers may be used in appropriate combination in order to achieve desired viscosity and physical properties.

In the present invention, as necessary, the elastomer may contain various additives such as a filler, an antioxidant, a fire retardant, an antimicrobial agent, a light stabilizer, a coloring agent, a flow improver, a lubricant, an antiblocking agent, an antistatic agent, a crosslinking agent, and a crosslinking aid, and these additives may be used singly or in combination of two or more of them. As long as the performance of the elastomer of the present invention is not impaired, the elastomer may contain additional various thermoplastic resins, thermosetting resins, thermoplastic elastomers, and others.

The impact-absorbing pad of the present invention may include an elastomer foam. Examples of the elastomer foam include a thermoplastic elastomer foam that is obtained by injection foaming of a foamable composition containing a thermoplastic elastomer and thermally expandable microcapsules. Here, the foamable composition contains thermally expandable microcapsules. The thermally expandable microcapsules are obtained by microencapsulation of a volatile liquid blowing agent with a polymer. Typically, the thermally expandable microcapsules can be produced by suspension polymerization of a polymerizable mixture containing at least a blowing agent and a polymerizable monomer in an aqueous medium. As the polymerization reaction proceeds, a resulting polymer forms an outer shell, and then the blowing agent is encapsulated in the outer shell to afford thermally expandable microcapsules.

The polymer usable for forming the outer shell is typically a thermoplastic resin having good gas barrier properties. A polymer forming the outer shell is softened by heat. The liquid blowing agent to be encapsuled in an outer shell resin is selected from materials that are transformed into a gas form at a softening point of the polymer or less.

The ratio of the thermally expandable microcapsules used in the present invention is preferably 0.5 part by weight or more and 10 parts by weight or less and more preferably 1 part by weight or more and 5 parts by weight or less with respect to 100 parts by weight of the foamable composition including the elastomer described above and a tackifier resin, a plasticizer, an additional resin, and other components that are contained as necessary. Thermally expandable microcapsules used in a ratio of less than 0.5 part by weight are unlikely to afford an injection foam-molded product that is excellent in lightweight properties and that has a density of 700 kg/m$^3$ or less. Conversely, even when the thermally expandable microcapsules are used in a ratio of 10 parts by weight or more, the density reaches saturation at about 350 kg/m$^3$ and the product is unlikely to obtain a lower density. The thermally expandable microcapsules are fine powder and thus are usually difficult to be homogeneously mixed. Moreover, the thermally expandable microcapsules involve risks such as a dust explosion. Hence, the thermally expandable microcapsules are preferably mixed as a masterbatch in which the thermally expandable microcapsules are dispersed at high concentration in a resin capable of being processed at a comparatively low temperature. In this case, the value obtained by multiplying the amount of a masterbatch by the content of thermally expandable microcapsules in the masterbatch is the amount of thermally expandable microcapsules.

A method for injection foaming of a foamable composition will next be specifically described. As the injection foam molding method itself, a known method can be applied, and a molding condition can be appropriately adjusted depending on the flowability of a foamable composition, the type of a molding machine, or the shape of a mold. In the case of the present invention, the injection foam molding is preferably carried out under a condition of a resin temperature of 170 to 250° C., a mold temperature of 10 to 100° C., a molding cycle of 1 to 120 minutes, an injection speed of 10 to 300 mm/second, an injection pressure of 10 to 200 MPa, and others. Various methods are known for foaming a composition in a mold. Among them, a so-called core back method (moving cavity method) in which a mold including a fixed mold and a movable mold movable forward and backward to a desired position is used, the movable mold is moved backward after the completion of injection, and then a composition is foamed is preferred because a non-foaming layer is formed on a surface, homogeneous fine bubbles are likely to be formed in an inside foaming layer, and an injection foam-molded product excellent in lightweight properties is readily obtained.

An elastomer foam that constitutes the impact-absorbing pad 10 and that uses expandable microcapsules as a foaming agent as above has characteristics of high closed cell ratio. For the reason, such a foam is unlikely to be compressed to the bottom in the case of impact, the load by the impact is unlikely to be largely increased, and hence the foam shows excellent impact absorbability. In the present invention, the elastomer foam has a closed cell ratio of 80% or more and preferably 90% or more.

The elastomer foam constituting the impact-absorbing pad 10 of the present invention preferably has a density of 100 kg/m$^3$ or more and more preferably 200 kg/m$^3$ or more. The density may be uniform or may be nonuniform in the pad main body 11. A pad main body 11 having a density of less than 100 kg/m$^3$ is required to have a large thickness in order to ensure impact absorbability, resulting in poor wearing comfort and poor external appearance.

As shown in FIG. 2, the impact-absorbing pad 10 of the present invention can be attached to a clothing main body 21 so as to apply the impact-deflecting part 12 onto the greater trochanter 1 of the femur, thereby composing clothing 20. Examples of the clothing main body 21 to which the impact-absorbing pad 10 is attached include, but are not necessarily limited to, boxer briefs, briefs, shorts, various pants for outerwear and sports, and trousers. Underpants are particularly preferred from the purpose of absorption of impact at an area susceptible to fractures. The impact-absorbing pad can also be attached to diapers and paper underpants. The method of attaching the impact-absorbing pad 10 is not particularly limited. The clothing main body 21 may have a pocket into which the impact-absorbing pad 10 is inserted in order not to displace the impact-absorbing pad 10 during wearing. In order not to cause the displacement, the impact-absorbing pad 10 may be sewn to the clothing main body 21 with a thread to be fixed. The impact-absorbing pad 10 may be in direct contact with a body or may be in indirect contact with a body through fabric. The pocket may be closed so that the impact-absorbing pad 10 cannot be taken out or may have a structure to put in and take out the absorbing pad 10 as desired. In place of the clothing main body 21, using a lumbar corset formed with a pocket capable of storing the impact-absorbing pad 10, while inserting and holding the impact-absorbing pad 10 in the pocket, the corset may be fixed to the lumbar region so as to apply the impact-deflecting part 12 onto the greater trochanter 1 of the femur. Alternatively, using a belt attached with a bag, while inserting and holding the impact-absorbing pad 10 in the bag, the impact-absorbing pad 10 may be fixed to a body with the belt so as to apply the impact-deflecting part 12 onto the greater trochanter 1 of the femur.

As required for easy installation and others, the impact-absorbing pad 10 of the present invention is used for the greater trochanter 1 of the femur and another pad may be used for a region where impact is comparatively relieved. Examples of another pad include a urethane foam pad, a polyethylene foam pad, an acrylic foam pad, a nonwoven fabric pad, and a three-dimensional fabric pad.

The material, the weave method, and the like of fabric used for the clothing are not particularly limited. For example, in order to improve breathability and impact absorbability, a fabric with an uneven surface may be used, and a knitted texture exposing an uneven shape on the surface, a pile-woven fabric, and other fabrics are preferred. In particular, it is revealed that the installation of such a fabric in the clothing on a body side can achieve the effects as above. In order to effectively relief impact by bringing the impact-absorbing pad 10 into close contact with a body, a stretch material may be used around the impact-absorbing pad 10.

<Evaluation of Impact Absorbability by Fall Simulation>

In the present invention, the impact absorbability of an impact-absorbing pad was evaluated by a computer simulation. A fall simulation by computer will be described hereinafter.

For a left femur model, using an individual femur modeling technique specifically described in Non-Patent Document 4 (Eiichi Tanaka et al.: Mechanical Study on Femoral Neck Fall Fractures by Finite Element Model Simulating Individual Differences, Transactions of the Japan Society of Mechanical Engineers (A), 70 (697), 1178-85, 2004), a left proximal femur model was prepared, then a soft tissue and a coxa were added to the left proximal femur model, and consequently the left femur model was constructed. The individual femur modeling technique uses 41 geometric parameters expressing morphological characteristics of the proximal femur and simply and immediately constructs a finite element model reflecting individual differences in the femur shape. In the present invention, the model was constructed using the mean value and the standard deviation of each geometric parameter determined from femur samples isolated from eight women from 53 years old to 89 years old.

Next, the cross sectional shape of the femoral soft tissue was closely approximated by an ellipse, and a membrane element simulating skin was disposed to the side face of the model. Corresponding to the shape of the femur head, the acetabulum that forms the coxa together with the femur head was constructed as a concentric hemisphere of a sphere closely resembling the bone head shape. The iliofemoral ligament, the pubofemoral ligament, and the ischiofemoral ligament that largely contribute to the stabilization of the coxa movement were modeled by a membrane element. The elements modeled by the technique above were combined to construct a left femur model, then others were constructed by a rigid element, and a lumped mass equal to the mass value of each segment was given to a calculated center of gravity of each part in a human body. A left lower leg was connected to the femur model.

Material characteristics of the left femoral model will next be described. Each of the cortical bone and the cancellous bone in the femur was an isotropic linear elastic medium, a muscle-adipose element of the femoral region was an isotropic Maxwell model, and a skin element was an isotropic linear elastic medium. The ligament element and the articular cartilage of the femoral head were also an isotropic linear elastic medium. Each of the muscle-adipose element, the skin element, the ligament element, and the cartilage element had a density of 1 g/cm$^3$. The acetabulum element had the material physical properties same as those of the cortical bone. Table 1 shows the characteristics of the materials used.

Based on the left femoral region finite element model prepared as above, the lumped mass was given to the center of gravity of each part in the whole body. Then, each part was connected using a rigid body as specifically described in Non-Patent Document 5 (Eiichi Tanaka et al.: Biodynamic Study on Prevention of Femoral Neck Fall Fractures by Hip Protector, Transactions of the Japan Society of Mechanical Engineers (A), 70 (697), 1193-1200, 2004), thereby to prepare a simple human body model that reproduced the mass distribution of a human body and that was to be used. A ground model simulating the ground parallel to the femur finite element model was disposed, then the simple human body model was given by a translational velocity of 2.75 m/s that was the velocity actually applied in a wall-normal direction in case of a fall, and a fall was simulated. The ground model was a cubic isotropic linear elastic medium having a side length of 300 mm, had material constants of concrete shown in Table 1, and had a mass density of 2.3 g/cm$^3$. A ground model surface that is not in contact with the femur was a stress non-reflecting boundary, and the displacement of the ground model was restricted.

TABLE 1

Material Characteristics of Human Body Model Used for Simulation

| | | E (MPa) | v | Viscosity (MPa · s) |
|---|---|---|---|---|
| | Muscle-adipose | 15 | 0.49 | 10 |
| | Skin | 10 | 0.3 | — |
| | Ligament | 285 | 0.3 | — |
| | Cartilage | 50 | 0.3 | — |
| | Acetabulum | 8400 | 0.3 | — |
| Cortical bone | Shaft | 13376 | 0.31 | — |
| | Trochanter | 9152 | 0.31 | — |
| | Lower neck base | 13376 | 0.31 | — |
| | Upper neck base | 11968 | 0.31 | — |
| | Lower bone head base | 11968 | 0.31 | — |
| | Upper bone head base | 8448 | 0.31 | — |
| | Femoral head | 8448 | 0.31 | — |
| Cancellous bone | Lower shaft | 145 | 0.29 | — |
| | Lower trochanter | 195 | 0.29 | — |
| | Upper trochanter | 253 | 0.29 | — |
| | Lower neck base | 190 | 0.29 | — |

TABLE 1-continued

Material Characteristics of Human Body Model Used for Simulation

| | E (MPa) | v | Viscosity (MPa · s) |
|---|---|---|---|
| Upper neck base | 395 | 0.29 | — |
| Lower bone head base | 300 | 0.29 | — |
| Upper bone head base | 374 | 0.29 | — |
| Femoral head | 420 | 0.29 | — |
| Ground (concrete) | 24500 | 0.2 | — |

A finite element analysis program LS-DYNA (Livermore Software Technology Corp., USA) was used for the analysis. A modeled shape of the impact-absorbing pad was attached to the femur model. Then, the fall simulation was carried out and a principal compressive stress applied to the femoral neck was calculated.

The material parameter of the impact-absorbing pad was calculated as a real material was subjected to a compression test under three conditions in which the speed varied and then the obtained stress-strain curve was used to be integrated as a material model for calculation. The material model was expressed by LS-DYNA low-density urethane material model (LOW_DENSITY_FOAM). The size of the impact-absorbing pad varied depending on Examples and each impact-absorbing pad was curved at a curvature radius of 60 mm so as to be along the femoral.

The compression test of the real material was carried out by cutting out a sample having any thickness into a round shape with a diameter of 30 mm and using a texture analyzer (manufactured by EKO Instruments Co., Ltd.) under three conditions at speeds of 5, 50, and 500 mm/min, therefore obtaining a stress-strain curve.

It is believed that a typical elderly women breaks a bone at a principal compressive stress of about 140 to 260 MPa, which varies depending on the bone density. In the present invention, the evaluation was carried out as a threshold level of 200 MPa.

<Density Measurement>

A material was cut out into a 20 mm square. Each side length was measured, and the volume was calculated. The measurement weight was divided by the volume to determine the density.

<Wearing Comfort Evaluation>

The evaluation of wearing comfort was performed as follows: an underpants having a pocket was produced so as to dispose an impact-deflecting part right above the greater trochanter 1 of the femur; in the pocket, an impact-absorbing pad was installed; ten public panelists worn the underpants for 24 hours to perform sensory evaluation on three points of "stuffy feeling", "uncomfortable feeling at the time of putting on and taking off (including at the time of putting on and taking off in a bathroom)", and "funny external appearance." The criteria are as below. The mean value was calculated based on the score of each panelist and was regarded as the evaluation score.

"Stuffy Feeling"

A: There are no stuffy feeling and no discomfort.
B: There are little stuffy feeling and little discomfort.
C: There is no opinion.
D: There are stuffy feeling and discomfort.

"Uncomfortable Feeling at the Time of Putting On and Taking Off"

A: There are no obstacle and no uncomfortable feeling at the time of putting on and taking off.

B: There are little obstacle and little uncomfortable feeling at the time of putting on and taking off.

C: There is no opinion.

D: There are obstacle and uncomfortable feeling at the time of putting on and taking off.

"External Appearance"

B: There is little appearance of the impact-absorbing pad when seen over the clothes.

C: There is no opinion.

D: There is the appearance of the impact-absorbing pad when seen over the clothes.

EXAMPLE 1

As Example 1, NP gel (foam gel) (manufactured by Taica Corporation) was used to produce an impact-absorbing pad that had a rectangular shape with a longitudinal length of 140 mm and a transverse length of 120 mm, had a thickness of 12 mm, and included an impact-deflecting part 12 having a through hole with a diameter of 50 mm, as the impact-absorbing pad 10A shown in FIG. 3(*a*).

EXAMPLE 2

As Example 2, an impact-absorbing pad was produced in a similar manner to the impact-absorbing pad in Example 1 except that the thickness was 8 mm.

EXAMPLE 3

Impact-absorbing pads of Examples 3 to 5 were evaluated using the elastomer foam below.

With respect to a mixture of 100 parts by weight of elastomer having a polystyrene block, a polyisobutylene block, and a polystyrene block, SIBSTAR 072T (manufactured by Kaneka Corporation) and 18 parts by weight of hydrogenated petroleum resin, ARKON P140 (manufactured by Arakawa Chemical Industries, Ltd.) as a tackifier resin, 10 parts by weight of thermally expandable microcapsule masterbatch, FINECELL MASTER MS405K (manufactured by Dainichiseika Color & Chemicals Mfg. Co., Ltd., a thermally expandable microcapsule content of 40 wt %) was mixed (the heat-expandable capsule mixing amount was 4 parts by weight) to prepare a foamable composition. The foamable composition was melted and kneaded with an injection molding machine, "MD350S-IIIDP type" (shutoff nozzle specifications) manufactured by Ube Machinery Corporation, Ltd. at a resin temperature of 200° C. and a back pressure of 15 MPa, and then was injected and filled at an injection speed of 100 mm/second into a mold that was set at 60° C., had a pin gate with a diameter cp of 2 mm, and included a fixed mold and a movable mold movable forward and backward that formed a box-shaped cavity having a longitudinal length of 330 mm, a transverse length of 230 mm, and a height of 100 mm (vertical wall section: a tilt angle of 10°, a clearance of 3 mm; bottom face section: a clearance t0=3.0 mm). After the completion of injection and filling, the movable mold was moved backward so that the bottom face section had a clearance of 6.5 mm, and the resin in the cavity was foamed. After the completion of foaming, the resulting foam was cooled for 60 seconds, and then the elastomer foam was taken out. The bottom of the box was cut out, and the compression test was carried out.

As Example 3, the elastomer foam was used to produce an impact-absorbing pad that had a rectangular shape with a longitudinal length of 140 mm and a transverse length of 120 mm, had a thickness of 12 mm, and included an impact-deflecting part 12 having a through hole with a diameter of 50 mm, as the impact-absorbing pad 10A shown in FIG. 3(*a*), in the same manner as in Example 1.

EXAMPLE 4

As Example 4, the elastomer foam was used to produce an impact-absorbing pad that included a first relief part 13B having a rectangular-shaped through hole with a longitudinal length of 6 mm and a transverse length of 75 mm and having the upper end at a position 22 mm distant from the lower end of the impact-deflecting part 12 in the impact-absorbing pad of Example 3, as the impact-absorbing pad 10B shown in FIG. 3(*b*).

EXAMPLE 5

As Example 5, the elastomer foam was used to produce an impact-absorbing pad that included a first relief part 13C having a through hole with a longitudinal length of 6 mm and a transverse length of 18 mm and having the upper end at a position 6 mm distant from the lower end of the impact-deflecting part 12 in the impact-absorbing pad of Example 3 and that further included another first relief part 13C having a through hole with the same shape as the through hole above and having the upper end at a position 6 mm distant form the lower end of the first relief part 13C above, as the impact-absorbing pad 10C shown in FIG. 3(*c*).

EXAMPLE 6

In Example 6, the elastomer foam used was prepared in a similar manner to that in Example 3 except that the elastomer having a polystyrene block, a polyisobutylene block, and a polystyrene block in Example 3 was replaced by SIBSTAR 062T (manufactured by Kaneka Corporation) as the material. An impact-absorbing pad of Example 6 had an elliptical shape with a long side length of 170 mm and a short side length of 130 mm and had a thickness of 8 mm as the impact-absorbing pad 10 shown in FIG. 3(*d*). The impact-absorbing pad 10 included an impact-deflecting part 12 having a through hole with a diameter of 50 mm and having the upper end at a position 40 mm distant from the upper end of the impact-absorbing pad 10. The impact-absorbing pad 10 also included a first relief part 13 having a through hole with a diameter of 20 mm and having the upper end at a position 15 mm distant from the lower end of the impact-deflecting part 12 and further included another first relief part 13 having a through hole with a diameter of 20 mm and having the upper end at a position 10 mm distant from the lower end of the first relief part 13 above. The impact-absorbing pad 10 also included a second relief part 14 having a through hole with a diameter of 30 mm and having the left end at a position 14 mm distant from the right end on the center line of the first relief part 13 in a transverse direction and further included another second relief part 14 having a through hole with a diameter of 30 mm and having the right end at a position 14 mm distant from the left end of the first relief part 13.

EXAMPLE 7

As Example 7, an impact-absorbing pad having the same structure as that of the impact-absorbing pad of Example 6 was prepared except that the thickness was 5 mm.

EXAMPLE 8

In Example 8, to 100 parts by weight of elastomer, SIBSTAR 072T (manufactured by Kaneka Corporation) as the material, 10 parts by weight of thermally expandable microcapsule masterbatch, FINECELL MASTER MS405K (manufactured by Dainichiseika Color & Chemicals Mfg. Co., Ltd., a thermally expandable microcapsule content of 40 wt %) was mixed (the heat-expandable capsule mixing amount was 4 parts by weight) to prepare a foamable composition, and an elastomer foam obtained in a similar manner to that in Example 3 was used. An impact-absorbing pad of Example 8 had a rectangular shape having a longitudinal length of 140 mm and a transverse length of 120 mm, had a thickness of 8 mm, and included an impact-deflecting part 12 having a through hole with a diameter of 50 mm, as the impact-absorbing pad 10A shown in FIG. 3(*a*).

EXAMPLE 9

In Example 9, an elastomer, SIBSTAR 072T (manufactured by Kaneka Corporation) was used as the material and was subjected to press molding at 200° C. to afford a plate having a thickness of 8 mm. Then, the plate was cut into a rectangular shape having a longitudinal length of 140 mm and a transverse length of 120 mm, then an impact-deflecting part 12 having a through hole with a diameter of 50 mm was formed, and an impact-absorbing pad was consequently produced as the impact-absorbing pad 10A shown in FIG. 3(*a*).

COMPARATIVE EXAMPLE 1

The principal compressive stress to the femoral neck 2 when no impact-absorbing pad was used was calculated.

COMPARATIVE EXAMPLE 2

As Comparative Example 2, a pad used in a hip protector (manufactured by Gunze Limited) was taken out to produce an impact-absorbing pad having a rectangular shape with a longitudinal length of 170 mm, a transverse length of 140 mm, and a thickness of 12 mm as with the real pad size and having no hole, as the impact-absorbing pad 30A shown in FIG. 4(*a*).

COMPARATIVE EXAMPLE 3

As Comparative Example 3, an impact-absorbing pad was produced in a similar manner to that in Comparative Example 2 except that the thickness was 5 mm.

COMPARATIVE EXAMPLE 4

As Comparative Example 4, the material same as that of the impact-absorbing pad of Example 4 was used to produce an impact-absorbing pad having a rectangular shape with a longitudinal length of 140 mm and a transverse length of 120 mm and having a thickness of 12 mm, as with Example 4, but having no impact-deflecting part 12, as the impact-absorbing pad 30B shown in FIG. 4(*b*).

COMPARATIVE EXAMPLE 5

As Comparative Example 5, an impact-absorbing pad was produced in a similar manner to that in the impact-absorbing pad of Example 4 except that an impact-deflecting part 31C with a diameter of 20 mm was formed in place of the impact-deflecting part 12, as the impact-absorbing pad 30C shown in FIG. 4(*c*).

COMPARATIVE EXAMPLE 6

As Comparative Example 6, an impact-absorbing pad used in cushion underpants (manufactured by Tokyo angel Corporation) was evaluated. The impact-absorbing pad of Comparative Example 6 had an elliptical shape with a longitudinal length of 160 mm, a transverse length of 120 mm, and a thickness 20 mm, as the impact-absorbing pad 30D shown in FIG. 4(*d*).

COMPARATIVE EXAMPLE 7

As Comparative Example 7, an impact-absorbing pad was produced in a similar manner to that in the impact-absorbing pad of Example 6 except that the thickness was 14 mm.

COMPARATIVE EXAMPLE 8

As Comparative Example 8, an impact-absorbing pad was produced in a similar manner to that in the impact-absorbing pad of Example 6 except that the thickness was 12 mm and the impact-deflecting part 12 had a diameter of 90 mm.

Examples 1 to 9 and Comparative Examples 1 to 8 were subjected to the evaluation test described above, and the obtained results are shown in Table 2.

TABLE 2

| | | Unit | Results | | | | | |
|---|---|---|---|---|---|---|---|---|
| | | | Example 1 | Example 2 | Example 3 | Example 4 | Example 5 | Example 6 |
| Pad size | Shape | | Rectangle | Rectangle | Rectangle | Rectangle | Rectangle | Ellipse |
| | Longitudinal length | mm | 140 | 140 | 140 | 140 | 140 | 170 |
| | Transverse length | mm | 120 | 120 | 120 | 120 | 120 | 130 |
| | Thickness | mm | 12 | 8 | 12 | 12 | 12 | 8 |
| Density | | kg/m$^3$ | 294.1 | 294.1 | 285.7 | 530 | 530 | 588.2 |
| Area of impact-deflecting part | | mm$^2$ | 1963.5 | 1963.5 | 1963.5 | 1963.5 | 1963.5 | 1963.5 |
| First and second relief parts | | | None | None | None | 6 × 75 mm rectangular hole | Two 6 × 18 mm rectangular arranged vertically | Two holes with a diameter of 20 mm arranged vertically and two holes with a diameter of 30 mm, one in the right side and the other in the left side of the holes arranged vertically |

TABLE 2-continued

| | | | | Results | | | | |
|---|---|---|---|---|---|---|---|---|
| Result | Maximum principal compressive stress by | MPa | 189.0 | 196.6 | 151.6 | 150.0 | 138.7 | 172.8 |
| Wearing comfort | Stuffy feeling | | C | C | C | B | A | A |
| | Uncomfortable feeling when putting on and taking off | | C | B | C | B | B | B |
| | External appearance | | C | B | C | C | C | B |

| | | Unit | Example 7 | Example 8 | Example 9 | Comparative Example 1 | Comparative Example 2 | Comparative Example 3 |
|---|---|---|---|---|---|---|---|---|
| Pad size | Shape | | Ellipse | Rectangle | Rectangle | — | Rectangle | Rectangle |
| | Longitudinal length | mm | 170 | 140 | 140 | — | 170 | 170 |
| | Transverse length | mm | 130 | 120 | 120 | — | 140 | 140 |
| | Thickness | mm | 5 | 8 | 8 | — | 12 | 5 |
| Density | | kg/m$^3$ | 588.2 | 520 | 1000 | — | 285.7 | 285.7 |
| Area of impact-deflecting part | | mm$^2$ | 1963.5 | 1963.5 | 1963.5 | — | — | — |
| First and second relief parts | | | Two holes with a diameter of 20 mm arranged vertically and two holes with a diameter of 30 mm, one in the right side and the other in the left side of the holes arranged vertically | None | None | — | None | None |
| Result | Maximum principal compressive stress by | MPa | 171.4 | 199.0 | 168.7 | 357.1 | 321.0 | 332.0 |
| Wearing comfort | Stuffy feeling | | A | C | C | — | D | D |
| | Uncomfortable feeling when putting on and taking off | | A | C | C | — | D | C |
| | External appearance | | B | B | B | — | C | B |

| | | Unit | Comparative Example 4 | Comparative Example 5 | Comparative Example 6 | Comparative Example 7 | Comparative Example 8 |
|---|---|---|---|---|---|---|---|
| Pad size | Shape | | Rectangle | Rectangle | Ellipse | Ellipse | Ellipse |
| | Longitudinal length | mm | 140 | 140 | 160 | 140 | 140 |
| | Transverse length | mm | 120 | 120 | 120 | 120 | 120 |
| | Thickness | mm | 12 | 12 | 20 | 14 | 12 |
| | Density | kg/m$^3$ | 530 | 530 | 52.1 | 588.2 | 588.2 |
| | Area of impact-deflecting part | mm$^2$ | — | 314.2 | — | 1963.5 | 6361.7 |
| | First and second relief parts | | None | None | None | None | None |
| Result | Maximum principal compressive stress by | MPa | 287.5 | 256.7 | — | — | 357.1 |
| Wearing comfort | Stuffy feeling | | D | D | D | D | C |
| | Uncomfortable feeling when putting on and taking off | | D | D | D | D | C |
| | External appearance | | C | C | D | D | C |

Table 2 shows that the pads with no impact-deflecting part as in Comparative Examples 1 to 4 had higher maximum principal compressive stress by simulation than those of the pads of Examples 1 to 8, and the pad having the impact-deflecting part with a smaller area had a high maximum principal compressive stress as shown by Comparative Example 5. This reveals that such a pad as in Comparative Examples 1 to 5 cannot sufficiently absorb the impact force to the greater trochanter of the femur.

Meanwhile, also in Examples 1 to 8, the pads in Examples 1 to 3, 8, and 9 including no first relief part and no second relief part having a through hole were likely to cause stuffy feeling, and uncomfortable feeling was caused at the time of putting on and taking off unless a pad had a low density and a small thickness as in Example 2. This reveals that the first relief part and the second relief part having a through hole are preferably formed as in Examples 4 to 7. Considering the external appearance in use, the thickness is preferably designed to be 8 mm or less as in Examples 6 and 7.

REFERENCE SIGNS LIST

1 Greater trochanter of femur
2 Femoral neck
3 Shaft of femur
10 Impact-absorbing pad
11 Pad main body
12 Impact-deflecting part
13 First relief part
14 Second relief part
20 Clothing
21 Clothing main body
10A Impact-absorbing pad
10B Impact-absorbing pad
13B First relief part
10C Impact-absorbing pad
13C First relief part
30A Impact-absorbing pad
30B Impact-absorbing pad
30C Impact-absorbing pad
31C Impact-deflecting part
30D Impact-absorbing pad

The invention claimed is:

1. An impact-absorbing pad comprising a pad main body having a flat shape, the pad main body including an impact-deflecting part having a through hole with a maximum length of 80 mm or less and an area of 600 mm² or more and 5,000 mm² or less such that the pad main body is configured to surround a greater trochanter of a femur, the pad main body being configured to apply the impact-deflecting part onto the greater trochanter of the femur such that the pad main body and a periphery of the greater trochanter of the femur facing the pad main body absorb an impact force directed to the greater trochanter of the femur, thereby preventing a femoral fracture, wherein the pad main body has a thickness of 13 mm or less, impact absorbability, and a flexural modulus of 100 MPa or less that is calculated based on a measurement in accordance with Japanese Industrial Standard (JIS) K7171, and the pad main body includes at least one first relief part having a through hole below the impact-deflecting part, a distance from a lower end of the impact-deflecting part to an upper end of the first relief part is 5 mm or more and 50 mm or less, and the first relief part is designed to have a maximum length of 5 mm or more and 50mm or less.

2. The impact-absorbing pad according to claim 1, wherein a distance from an upper end of the impact-deflecting part to an upper end of the pad main body is designed to be 10 mm or more.

3. The impact-absorbing pad according to claim 1, wherein two first relief parts are arranged vertically.

4. The impact-absorbing pad according to claim 1, wherein the pad main body includes a second relief part having at least one through hole, and the second relief part has an area of 50% or less of a total area of the pad main body except the impact-deflecting part and the first relief part.

5. The impact-absorbing pad according to claim 1, wherein the pad main body includes an elastomer, and the elastomer is an isobutylene block copolymer including a polymer block having isobutylene as a constituent monomer and a polymer block having an aromatic vinyl monomer as a constituent monomer.

6. The impact-absorbing pad according to claim 5, wherein the elastomer contains a tackifier resin.

7. The impact-absorbing pad according to claim 1, wherein the pad main body includes an elastomer foam.

8. The impact-absorbing pad according to claim 1, wherein a chamfered face is formed on at least a corner of an outer peripheral edge of the pad main body.

9. Clothing comprising the impact-absorbing pad according to claim 1, the impact-absorbing pad being attached to a main body of the clothing to apply the impact-deflecting part of the impact-absorbing pad onto the greater trochanter of the femur.

10. The clothing according to claim 9, wherein the impact-absorbing pad is removably attached to the clothing main body.

11. The clothing according to claim 9, wherein the clothing main body is underpants.

12. A method for preventing a femoral fracture comprising attaching the impact-absorbing pad according to claim 1 to apply the impact-deflecting part of the impact-absorbing pad onto the greater trochanter of the femur.

\* \* \* \* \*